United States Patent [19]

Kida et al.

[11] Patent Number: 4,791,052

[45] Date of Patent: Dec. 13, 1988

[54] SILVER HALIDE PHOTOGRAPHIC LIGHT-SENSITIVE MATERIAL

[75] Inventors: Shuji Kida; Noritaka Nakayama, both of Hino; Katsunori Katoh; Takako Tanaka, both of Hachioji; Satoshi Nakagawa, Sagamihara; Kosaku Masuda, Akishima, all of Japan

[73] Assignee: Konishiroku Photo Industry Co., Ltd., Tokyo, Japan

[21] Appl. No.: 30,510

[22] Filed: Mar. 27, 1987

[30] Foreign Application Priority Data

Mar. 29, 1986 [JP] Japan .................................. 61-72351

[51] Int. Cl.[4] ................................................ G03C 7/38
[52] U.S. Cl. .................................... 430/558; 430/386; 430/387
[58] Field of Search ........................ 430/558, 386, 387

[56] References Cited

U.S. PATENT DOCUMENTS

| | | | |
|---|---|---|---|
| 4,548,899 | 10/1985 | Nakayama et al. | 430/558 |
| 4,588,679 | 5/1986 | Furutachi | 430/558 |
| 4,623,617 | 11/1986 | Kaneko et al. | 430/558 |
| 4,684,603 | 8/1987 | Nishijima et al. | 430/558 |
| 4,695,530 | 9/1987 | Nakamura et al. | 430/386 |

*Primary Examiner*—Paul R. Michl
*Assistant Examiner*—Mark R. Buscher
*Attorney, Agent, or Firm*—Finnegan, Henderson, Farabow, Garrett & Dunner

[57] ABSTRACT

A silver halide photographic light-sensitive material containing a 1H-pyrazolo[3,2-c]-s-triazole type magenta coupler is disclosed. The magenta coupler has an —$SO_2$— group and at least one group selected from the group consisting of a —COOM group and a —$SO_3M$ group, M being a hydrogen atom or a cation, in its molecule. The photographic material is improved in color development performance and preservability of magenta images.

5 Claims, No Drawings

SILVER HALIDE PHOTOGRAPHIC LIGHT-SENSITIVE MATERIAL

FIELD OF THE INVENTION

The present invention relates to a silver halide photographic light-sensitive material containing a magenta coupler, in particular, to the silver hoaide photographic light-sensitive material containing a novel magenta coupler having pyrazolotriazole and being capable of producing a dye-image excellent in color development performance and preservability.

BACKGROUND OF THE INVENTION

Among silver halide photographic light-sensitive materials, the known couplers generally used include an open-chined ketomethylene type yellow couplers, a pyrazolone type or pyrazoloazole type couplers and a phenol or naphthol type cyan couplers.

Conventionally, pyrazolone compounds have been frequently employed as magenta couplers. The pyrazolone type magenta couplers are disclosed, for example, in U.S. Pat. Nos. 2,600,788 and 3,519,429, Japanese Patent Publications Open to Public Inspection (hereinafter referred to as Japanese Patent O.P.I. Publications) Nos. 111631/1974 and 35858/1982, and the like. However, as described in"The theory of the photographic process" published by Mcmillan & Co., 4th edition (1977), pp 356-358, "Fine Chemical" published by CMC, vol. 14 No. 8, pp 38-41, and the excepts of lectures, pp 108-110, in the annual convention of the Photographic Society of Japan in 1985 (May 23, 1985 at Shigaku-Kaikan Hall in Tokyo), the dye formed from a pyrazolone type magenta coupler has an undesirable secondary absorption, which has gathered a need for improvement thereof.

As the above-mentioned literatures describe, a dye produced from a pyrazolotriazole type magenta coupler does not have such a secondary absorption. The fact that this coupler is an advantageous is disclosed, other than the literatures, above, in U.S. Pat. Nos. 3,810,761, 3,758,309 and 3,725,067.

However, even such an excellent magenta coupler is insufficient in color forming properties which relates to a density and contrast of the color image and a sensitivity of the light-sensitive material and, additionally, the preservability of a dye formed from the coupler is also insufficient.

SUMMARY OF THE INVENTION

It is a object of the present invention to provide a silver halide photographic light-sensitive material being capable of producing a magenta dye-image having excellent color forming properties as well as preservability.

The above-mentioned object of the invention is accomplished by a silver halide light-sensitive material comprising a support and at least one silver halide emulsion layer provided thereon, wherein said emulsion layer contains a 1H-pyrazolo[3,2-c]-s-triazole type magenta coupler having —$SO_2$— group and one group selected from —COOM and—$SO_3M$ group, M is a hydrogen atom or a cation, in its molecule.

DETAILED DESCRIPTION OF THE INVENTION

The 1H-pyrazolo[3,2-c]-s-triazole type magenta coupler of the invention is characterized by the inclusion within its molecular structure of both at least one group selected from —COOM and —$SO_3M$, and —$SO_2$—, and may have for example, at least on group selected from —COOM and —$SO_3M$, and —$SO_2$— in the third and in sixth positions of 1H-pyrazolo[3,2-c]nucleus respectively; or, the coupler may simultaneously have whichever in the third or sixth position at least one group selected from —COOM and —$SO_3M$, and —$SO_2$—. However the preferable magenta coupler of the invention is one simultaneously having whichever in the third or sixth position both at least one group selected from —COOM and —$SO_3M$, and —$SO_2$—.

The most favorable magenta coupler of the invention is one represented by the following formulas [I] and [II].

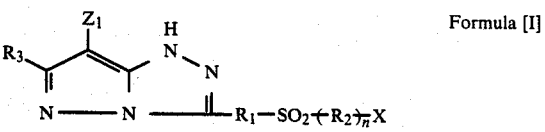

Formula [I]

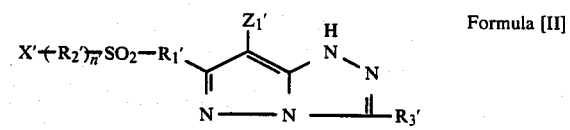

Formula [II]

In formula [I], $R_1$ and $R_2$ independently represent a bivalent bonding group. $R_3$ represents a hydrogen atom, alkyl group, aryl group, alkylthio group, acylamino group, alkoxy group,

(where, either $R_4$ or $R_5$ represents an alky group or an aryl group) or a heterocyclic group. X represents a monovalent group having —COOM or —$SO_3M$. $Z_1$ represents a group capable of being splitted off upon the reaction with the oxidized product of the color developing agent, and n represents 1 or 0.

In formula [II], each of $R_1'$, $R_2'$, $R_3'$, $R_4'$, $X'$, $Z_1'$ and n is the same as each of $R_1$, $R_2$, $R_3$, X, $Z_1$ and n in formula [I].

More specifically, in formulas [I]and [II], the examples of a bivalent bonding group represented by either $R_1$or $R_1'$ include, for example, and alkylene group, an arylene group, groups represented by —$NR_6$— where, $R_6$ represents either a hydrogen atom or an alkyl group,

or the like, and the groups formed by combining these groups.

The alkylene group may be whichever straight or branched chain structure, and is exemplified by a methylene group, ethylene group, trimethylene group, propylene group, dimethyethylene group, pentadecylmethylene group or the like. The arylene group is exemplified by a phenylene group, naphthylene group or the like, and, a phenylene group is preferable.

The examples of a group obtained by the combination of any of the above-mentioned groups-specifically include an aralkylene group

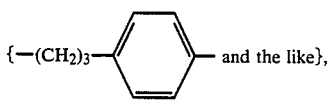 and the like},

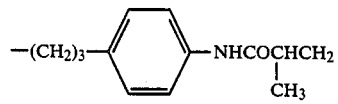

and the like.

The preferable bivalent bonding group represented by $R_1$ or $R_1'$ is an alkylene group, or, in particular, and alkylene group having 1-5 carbon atoms.

The bivalent bonding group represented by $R_2'$ in formulas [I] and [II] is exemplified by an alkelene group, an arylene group, any of groups represented by —O—,

(where, $R_6$ represents either a hydrogen atom or an alkyl group) or

any of groups formed by the combination of these groups.

The examples of such an alkylene group are the same as those of the alkylene group represented by $R_1$ or $R_1'$.

The examples of such an arylene group include a phenylene group, a naphthylene group and the like, and, among these a phenylene group is preferable. Those groups formed by the combination of the above-mentioned groups include a group represented by

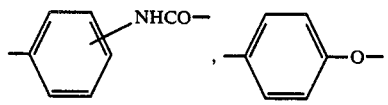

or the like, and, among these a group represented by

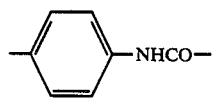

is preferable.

As the bivalent bonding group represented by $R_2$ or $R_2'$,

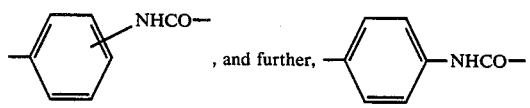

are preferable.

The examples of an alkyl group represented by $R_3$ or $R_3'$ in formulas [I] and [II] may be whichever straight or branched chain ones, and include a methyl group, ethyl group, propyl group, isopropyl group t-butyl group, pentadecyl group and the like. Furthermore, the alkyl groups represented by $R_3$ or $R_3$ may gave a substituent in the form of an alkoxy group, a carboxyl group or the like, and are exemplified by a methoxymethylgroup, ethoxydimethylmethyl group, carboxylnonyl group and the like.

The aryl group represented by either $R_3$ or $R_3'$ include a phenyl group, naphthyl group and the like, and, a phenyl group is preferable.

The alkylthio groups represented by either $R_3$ or $R_3'$ include a methylthio group, ehtylthic group and the like, and, a methylthic group is preferable.

The acylamino groups represented by either $R_3$ or $R_3'$ include the groups respectively represented by —NHCOCH$_3$, —NHCOC$_2$H$_5$, —NHCOC$_3$H$_7$, —NHCOC$_6$H$_5$ and the like, and, one represented by —NHCOC$_6$H$_5$ is preferable.

The alkoxy groups represented by either $R_3$ or $R_3'$ include a methoxy group, ehtoxy group, propoxy group and the like, and, an ethoxy group is preferable.

The groups represented by

which is also represented either by $R_3$ or $R_3'$ include an alkylamino group, for example, a dimethylamino group, a methylethylamino group, a diethylamono group or the like, an arylamino group, for example, an anilino group, a naphthylamino group or the like, and the like, and, both a dimethylamino group and an anilino group are preferable.

As a geterocyclic group represented by either $R_3$ or $R_3'$, 5~7 membered ones are preferable, and the examples of which include a 2-furyl group, 2-thienyl group, 2-pyrimidinyl group, 2-benzothiazolyl group and the like.

As $R_3$ or $R_3'$, an alkyl group is especially preferable.

As a monovalent group having —COOM or —SO$_3$M and represented by either X in formula [I] or X' in formula [II], the group represented either by —R$_7$—COOM or —R$_7$—SO$_3$M is preferable, where, $R_7$ represents either an alkylene group or an arylene group.

Such an alkylene group represented by $R_7$ may be whichever a straight or branched chain group, and may have a substituent. The examples of the similar group include a methylene group, ehtylene group, propylene group, 1-methylmethylene group, 1-octadecylethylene group, 1-dodecylmethylene group, 1-hexadecylethylene group and the like. Such an arylene group represented by $R_7$ is embodied by a phenylene group or the like.

As $R_7$ an alkylene group is especially advantageous.

M represents either a hydrogen atom or cation (for example, of an alkaline metal, an alkaline earth metal, a quaternary amine or the like), and, a hydrogen atom is especially advatageous.

The examples of a group capable of being splitted off upon the reaction with the oxidized product of the color developing agent and represented by either $Z_1$ in formula [I] or $Z_1'$ in formula [II] include a halogen atom, alkoxy group, aryloxy group, acyloxy group, arylthio group, alkylthio group,

($Z_2$ represents a plurality of atoms necessary to complete a five or six-membered ring together with a nitrogen atom as well as an atom selected from a carbon atom, an oxygen atom, a nitrogen atom and a sulfur atom) and the like.

The typical examples of the groups, abov, are as follows:

Halogen atom: chlorine atom, bromine atom, fluorine atom and the like;

Alkoxy group: ethoxy group, benzyloxy group, ethylcarbamoymethoxy group, tetradecylcarbamoylmethoxy group and the like;

Aryloxy group: phenoxy group, 4-methoxyphenoxy group, 4-nitrophenoxy group and the like;

Acyloxy group: acetoxy group, myristoyloxy group, benzoyloxy group and the like;

Arylthio group: phenylthio group, 2-butoxy-5-octylphenylthio group, 2,5-dihexyloxyphenylthio group and the like;

Alkylthio group: methylthio group, octylthio group, hexadecylthio group, benzylthio group, 2-(diethylamino) ethylthio group, ethoxycarbonylmethylthio group, ethoxyethylthio group, phenoxyethylthio group and the like:

The examples of those represented by

include the following

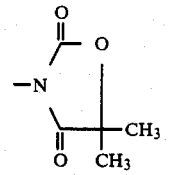

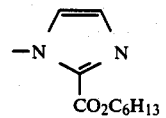

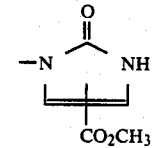

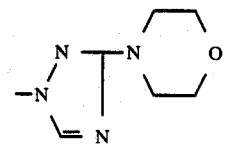

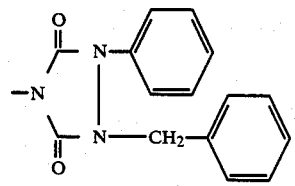

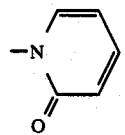

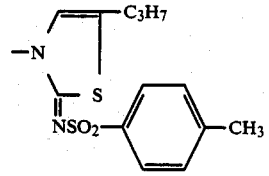

As the examples of $Z_1$ or $Z_1'$, halogen atoms are preferable, and, a chlorine atom is especially advantageous.

The typical examples of a magenta coupler according to the present invention are as follows. However, the invention is not limited only to these examples.

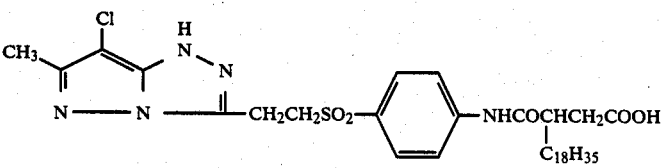

M-1

-continued
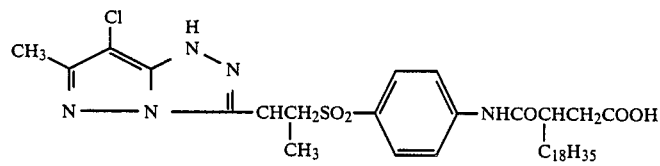
M-2
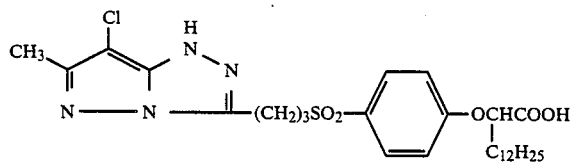
M-3
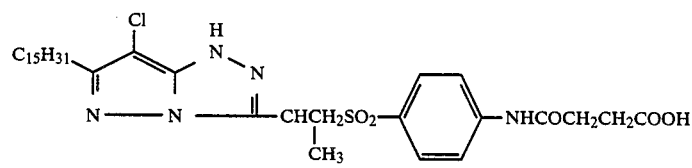
M-4
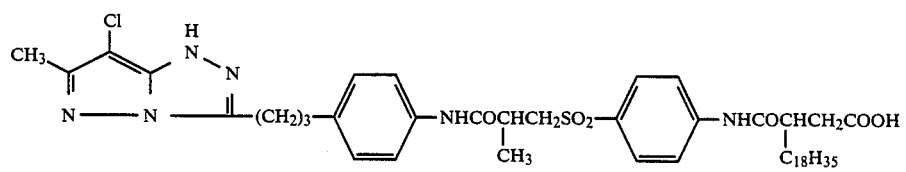
M-5
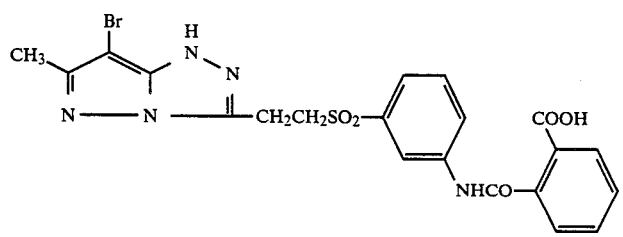
M-6
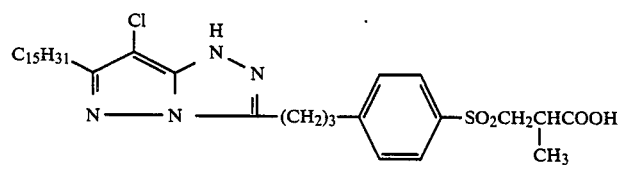
M-7
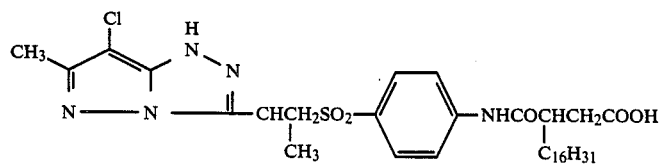
M-8
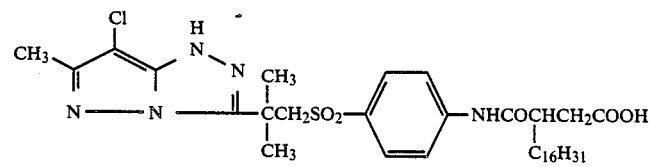
M-9
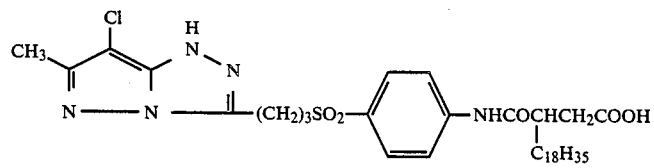
M-10

-continued
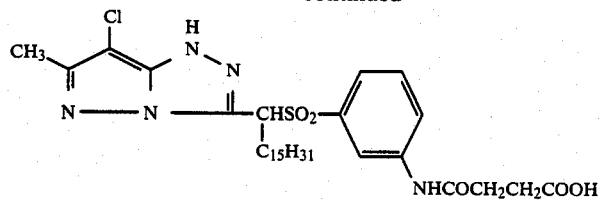
M-11
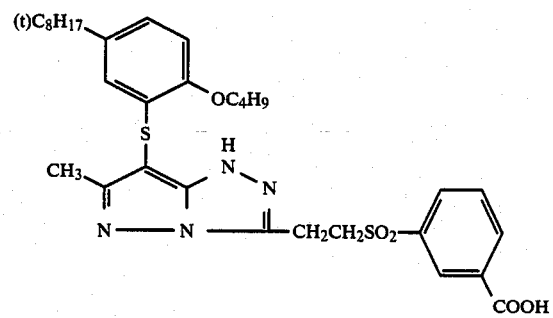
M-12
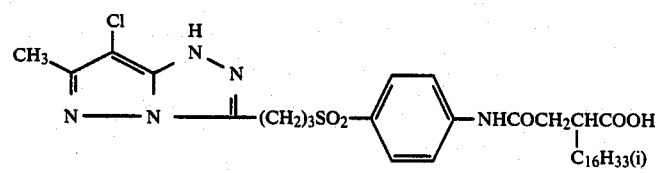
M-13
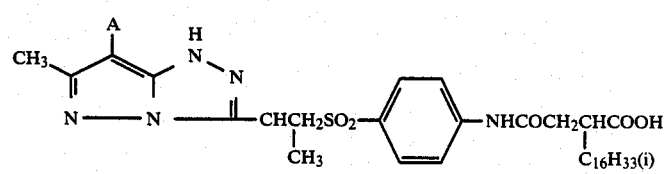
A
| | | | |
|---|---|---|---|
| —F | M-14 | 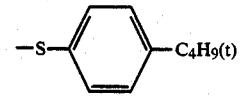 | M-15 |
| —SC$_{16}$H$_{33}$ | M-16 | —OCH$_2$C$_6$H$_5$ | M-17 |
| —OCH$_2$CONHC$_2$H$_5$ | M-18 | 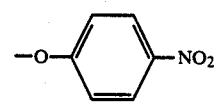 | M-19 |
| —OCOC$_6$H$_5$ | M-20 |  | M-21 |
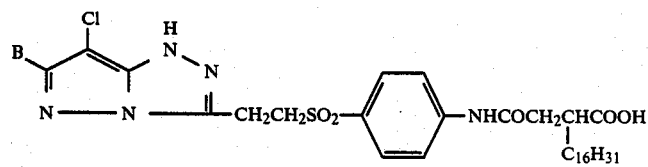
B
| | | | |
|---|---|---|---|
| —C$_2$H$_5$ | M-22 | —C$_3$H$_7$(i) | M-23 |
| —C$_4$H$_9$(t) | M-24 | —C$_{15}$H$_{31}$ | M-25 |

| | | |
|---|---|---|
| $\begin{array}{c}CH_3\\ -C-OC_2H_5\\ CH_3\end{array}$ M-26 | $-CH_2OCH_3$ | M-27 |
| $-(CH_2)_9COOH$ M-28 | (phenyl) | M-29 |
| $-SCH_3$ M-30 | $-N\begin{array}{c}CH_3\\ CH_3\end{array}$ | M-31 |
| $-NHC_6H_5$ M-32 | $-NHCOC_6H_5$ | M-33 |
| $-OC_2H_5$ | | M-34 |

M-35: $C_{12}H_{25}SO_2CH_2$-substituted pyrazolotriazole with chloro, linked via $-(CH_2)_3-$ to $-C_6H_4-NHCOCH_2CH_2COOH$ M-36: $CH_3$-substituted pyrazolotriazole with chloro, linked via $-CH_2CH_2SO_2-$ to $-C_6H_4-NHCOCHCH_2COOC_{10}H_{21}$ with $SO_3Na$ M-37: $H_{33}C_{16}CHCH_2CONH-$ with $COOH$, $-C_6H_4-SO_2CH_2CH_2CH_2-$ linked to chloro pyrazolotriazole with $-CH_3$ M-38: $(CH_3)_2CH-$ substituted chloro pyrazolotriazole, linked via $-CHCH_2SO_2-$ (with $CH_3$) to $-C_6H_4-NHCOCHCH_2COOH$ with $C_{16}H_{31}$ M-39: $(CH_3)_3C-$ substituted chloro pyrazolotriazole, linked via $-CHCH_2SO_2-$ (with $CH_3$) to $-C_6H_4-NHCOCHCH_2COOH$ with $C_{14}H_{27}$ The typical synthesis examples of a 1H-pyrazolo-[3,2-c]-s-triazole magenta coupler according to the invention are as follows.

Synthesis example 1: Semthesis of M-2

$CH_2=CCOOH + NO_2-C_6H_4-SH \xrightarrow[CH_3CHOOC_2H_5]{(CH_3CH_2)_3N, \text{ Hydroquinone}}$
$\quad\ |$
$\ \ CH_3$ -continued
Synthesis example 1: Semthesis of M-2

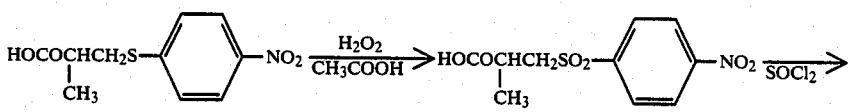
(1)

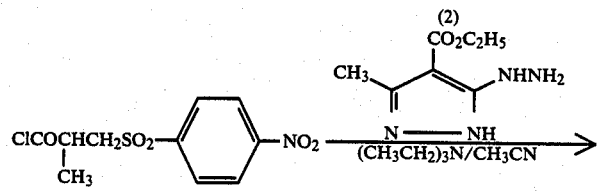
(3)

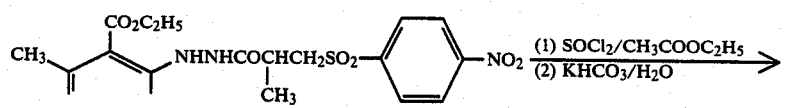
(4)

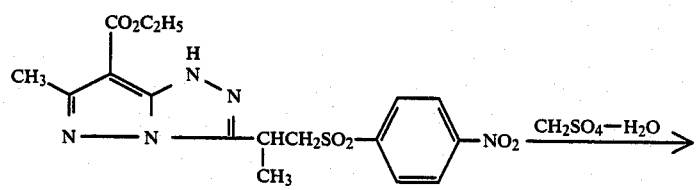
(5)

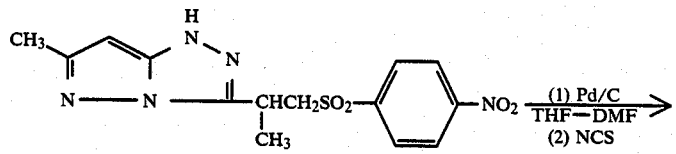
(6)

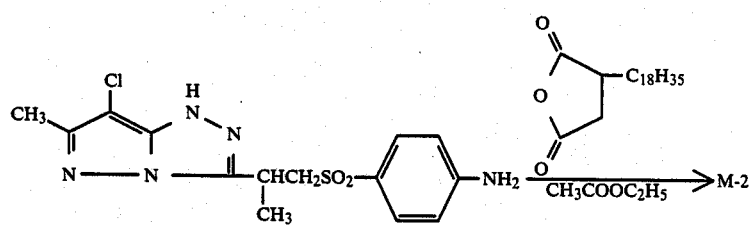
(7)

50 ml ethyl acetate was added to 17 g nitrothiophenol and 0.12 g hydroquinone, whereby 14 g methacrylic acid was added to dissolve the ingredients. Into the solution thus prepared, 2.2 g triethylamine was added dropwise in the time span of approximately ten minutes. The solution was then agitated for two hours under the room temperature. A solution prepared by dilluting 1.8 ml concentrated sulfuric acid with 10 ml water was added to this reaction solution, whereby the water layer being separated in the upper layer was removed, then the ethyl acetate layer was rinsed twice with water. The crystals deposited by concentrating the ethyl acetate layer to approximately 30 ml and cooling it to 6° C. was filtered off. In such a manner, 20.5 g of the compound represented by the above-mentioned formula (1) was prepared. The yield was 77.7%.

Next, to 16 g of the compound represented by the above-mentioned formula (1) was added 40 ml acetic acid, which was heated to 50°-60° C., whereby 25.8 g of 35% hydrogen peroxide was slowly added dropwise. Then, the solution was agitated for one hour at 80° C. The resultant reaction solution was chilled in an ice bath, depositing a solid material. 100 ml water was added to the solid material, which was then filtered off and rinsed with water to produce 14.6 g of the compound represented by the above-mentioned formula (2) in the form of pale yellow solid. The yield was 81%.

Next, 14.6 g of the compound represented by the above-mentioned formula (2) was heated and refluxed together with 20 ml thionyl chloride for two hours, then, subjected to vacuum concentration, producing an acid chloride (3).

Next, 50 ml acetonitrile and 6 g triethylamine were added to 9.9 g 3-methyl-4-ethoxycarbonyl-5-hydrazino-1H-pyrazole, which were heated and refluxed. During the refluxing, the above-mentioned acid chloride (3) was added dropwise. The solution was then further refluxed for five minutes, and subjected to vacuum concentration. 200 ml water and 200 ml ethyl acetate were added to the resultant residue, then the ethyl acetate layer was separated. The ethyl acetate layer was then dried with sodium sulfate anhydride and subjected to vacuum concentration. The resultant residue was recrystalized from the solvent containing mixture of ethyl acetate and hexane, thus producing 15 g of the compound represented by the above-mentioned formula (4). The yield was 64%.

Next, 100 ml ethyl acetate and 5.3 ml thionyl chloride were added to 10.7 g of the compound represented by the above-mentioned formula (4), which was then heated and refluxed for five hours. The solution was subjected to vacuum concentration, whereby 100 ml ethyl acetate was again added, thereupon, 70 ml aquenous potassium bicarbonate was further added, and heated and refluxed for one hour. The ethyl acetate layer was separed and rinsedtwice with water, and subjected to vacuum concentration. The solvent containing mixture of ethyl acetate and hexane was added to the resultant residue, depositing a solid material. The solid material was collected through filtration, producing 6.3 g of the compound represented by the above-mentioned formula (5). The yield was 62%.

Then, 3 ml concentrated sulfuric acid and 3 ml water added to 6.0 g of the compound expressed by the above-mentioned formula (5), whereby the solution was heated and refluxed for five hours. The reaction solution was poured into 50 ml ice water, whereby 50 ml ethyl acetate was added, then the ethyl acetate layer was separated off. The ethyl acetate layer was rinsed with water, and subjected to vacuum concentration. The solvent containing mixture of ethyl acetate and hexane was added to the resultant residue, and the deposited solid material was filtered off. In this way, 3.6 g of the compound represented by the abbve-mentioned formula (6) was produced. The yield was 73%.

Next, 3.5 g of the compound represented by the above-mentioned formula (6) was dissolved into the solution comprising 10 ml tetrahydrofuran (THF) and 10 ml (dimethylformamide), whereby 0.5 g of 5% palladium carbon (pd/C) was added, then the solution was subjected to catalytic hydrogenation. The palladium carbon was removed through filtration when the solution had absorbed a stoichiometric quantity of hydrogen, whereby 1.4 g N-chlorosuccinimide (NCS) was added into the filtrate. 50 ml ethyl acetate and 50 ml water were added into the reaction solution, then the ethyl acetate layer was separated. After being rinsed with water, the ethyl acetate layer was subjected to vacuum concentration, whereby the residue was purified with a silicagel chromatography, thus producing the compound represented by the above-mentioned formula (7). The yield was 61%.

Then, 30 ml ethyl acetate and 2.3 g octadecenyl succinic anhydride were added to 2.0 g of the compound represented by the above-mentioned formula (7), whereby the solution was heated and refluxed for two hours. The reaction solution was subjected to vacuum concentration, and the resultant residue was purified with a silicagel chromatography. The purified residue was then recrystalized from the solvent containing mixture of ethyl acetate and hexane, producing 2.4 g of the object compound (M-2). The yield was 60% at mp 139° and 141° C.

Synthesis: Synthesis of M-9

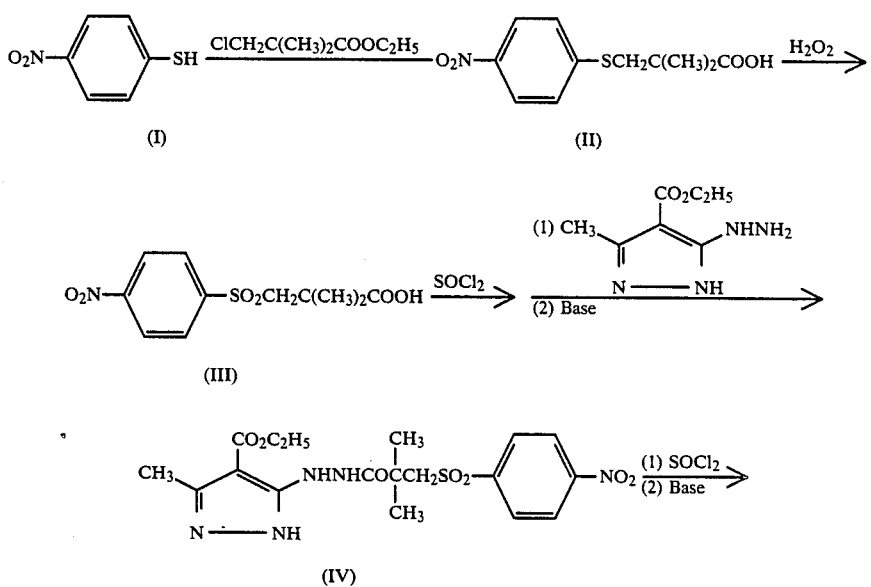

-continued
Synthesis: Synthesis of M-9

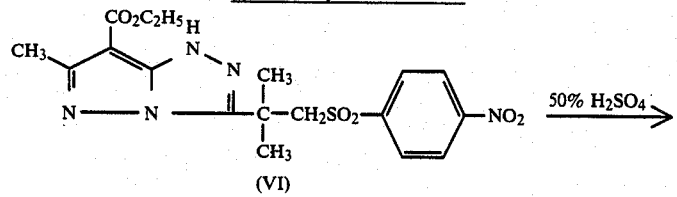

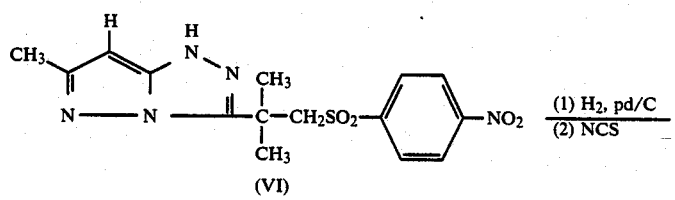

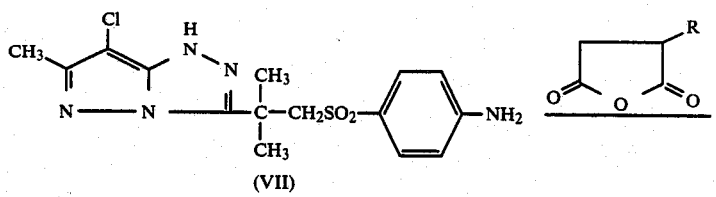

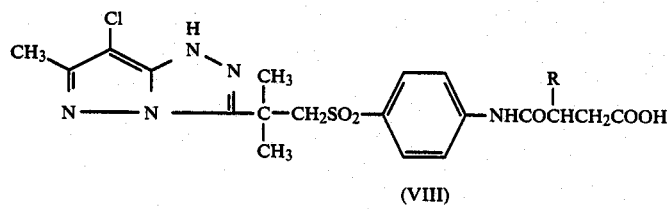

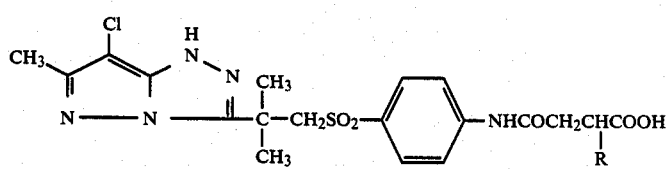

(R = C₁₆H₃₁)

(1) Synthesis of linking acid (III)

31 g of p-nitrothiophenol (I) as well as 32.9 g chloropinalic ester were dissolved into 250 ml Methyl cellosolve ©, whereby 19.2 g of 85% KOH was added, and the solution was refluxed for ten hours. After being let to cool, the insoluble matter was filtered off and rinsed with a small amount of toluene. The filtrate together with rinsing solution were concentrated, where 500 ml water was added. Concentrated sulfurinc acid was used to adjust the pH of solution to 1-2. After the extraction with ethyl acetate, the extract was dried with magnesium sulfate in order to distill out the ethyl acetate, and crystalized by means of 100 ml toluene, thus producing 15.6 g of yellow crystals (II). The yield was 30.6%.

Next, 9.5 g of the yellow crystals (II) was allowed to react with 15 ml of 35% hydrogen peroxide as well as 45 ml acetic acid for one hour in the presence of catalytic amount of Na₂WO₄. The reaction solution was concentrated to the extent that it was not completely dry and hard, then a little amount of ethyl acetate was added to the deposited solid material in order to collect the material through filtration, which produced 10 g of pale yellow-green solid material [III]. The yield was 93.5%.

(2) Synthesis of closed ring product [V]

After 20 g of the obtained linking acid [III] together with 15 ml thionyl chloride were heated and refluxed for five hours as dissolved in 100 ml chloroform, the solvent was distilled out. 200 ml chloroform and 12.8 g hydrazinopyrazole were added to the residue, which was refluxed for one hour as suspended in the solvent, then the solid material was collected through filtration. After being rinsed with ethyl acetate, the solid material as maintained moist was added into the solution comprising 8.4 g potassium bicarbonate, 100 ml water and 200 ml ethyl acetate, and heated for ten minutes, then the material dissolved itself after bubbling. By filtering off the resultant insoluble matter and by distilling out the solvent, 20.4 g acyl product (IV) was produced. The yield was 64.3%.

Then, 15.5 g of the acyl product (IV) as well as 7.2 ml thionyl chloride were refluxed for eitht hours as dissolved in 150 ml chloroform, then the solvent was distilled off under a normal pressure. 7 g pottassium bicarbonate, 50 ml water and ethyl 150 ml ethyl acetate were added to the resultant residue, then the solution was refluxed for two hours. The deposited solid material was collected through filtration to produce 11.9 g of the closed ring product (V). The yield was 80%.

(2) Synthesis of coupler (VII)

9 ml of 50% sulfuric acid was added to 8.9 g of the obtained closed ring product (V), whereby the solution was refluxed for two hours in a bath having a temperature of 120° C. When 50 m( water was added to the solution, the solid material deposited. The solid material was collected through filtration, rinsed with water and let to dry, thus producing 7.3 g of the compound represented by the formula (VI). The compound was a yellow solid material, and the yiels was 98.2%. 6 g of the obtained nitro product (VI) was dissolved into the solution containing a mixture of 18 ml dimethylformamide and 24 ml tetrahydrofuran, where 1 g of palladium carbon (Pd/C) was added and hydrogenated. Then, the palladium carbon (Pd/C) was removed through filtration. 2.24 g of 90% N-chlorsuccinimide (NCS) was added into the filtrate, which was agitated for one hour at a room temperature. Additionally, after 200 ml of water being added, extraction was effected with 150 ml ethyl acetate. The extract was dried with magenesium sulfide, then the solvent was distilled out to harden the extract, thus producing 5.45 g of the amino product (VII) in the form of pale prange solid material. The yield was 89.7%.

5 g of the amino product (VII) together with 4.2 g hedadecenyl succinic anhydride were refluxed for three hours as dissoved in 20 ml ethyl acetate, whereby 4.2 g hexadecenyl succinic anhydride was further added to the solution, which was further refluxed for three hours. After the solvent being distilled out, 4.1 g of the coupler (M-9) represented by the above-mentioned formula (VIII) was obtained through the crystalization from 50 g of acetonitrile. The yield was 42.6% at mp149 and 152° C.

The silver halide photographic light-sensitive material having the previously mentioned 1H-pyrazolo [3,2-C]-S-triazole series magenta coupler according to the invention (hereinafter referred to as the magenta coupler of the invention) may also contain the dye-forming couplers conventionally used in the art.

For example, the open chain ketomethylene series couplers which are yellow-dye-forming couplers conventionally known and used in the art can be used for this purpose. Among these, the pivaloylacetanilide series or benzoylacetanilide series couplers are advantageous. The typical examples of the usable yellow-dye-forming couplers are disclosed in U.S. Pat. Nos. 2,875,057, 1,077,874, 3,408,194 Japanese Patent O.P.I. Publications Nos. 123342/1975, 87650/1975, 133329/1979, Japanese Patent Examined Publication No. 19031/1971, Japanese Patent O.P.I. Publications Nos. 29432/1973, 66834/1973, 66835/1973, 94432/1973, 28834/1975, 99433/1979, 70841/1980, 74249/1981, Japanese Patent Examined Publication No. 19956/1970, Japanese Patent O.P.I. Publications Nos. 102636/1976, 87041/1981 and the like.

As a cyan-dye-forming coupler, phenol series compounds, naphthol series compounds and the like are available. The typical examples of them are disclosed in U.S. Pat. Nos. 2,369,929, 2,474,293, 2,772,162, 2,895,826, U.K. Pat. No. 1,038,331, Japanese Patent Examined Publication No. 36894/1973, Japanese Patent O.P.I. Publication No. 21139/1972, U.S. Pat. No. 3,737,316, Japanese Patent O.P.I. Publication No. 74844/1973, U.S. Pat. Nos. 3,880,661, 4,124,396 and 4,333,999, Japanese Patent O.P.I. Publications Nos. 21094/1980 112038/1975, 117422/1975, 18315/1977, 115230/1979, 163537/1980, 136650/1982, 155538/1982, 204545/1982, 32071/1980, 108662/1980, 1938/1981, 27147/1981, 80045/1981, 104333/1981, 65134/1981, 204544/1982, 98731/1983 and the like.

As a magenta-dye-forming coupler, one or more than two of the magenta couplers of the invention may be combinedly employed. Furthermore, the conventionally known pyrazolone series compounds, indazolone series compounds, cyanoacetyl series compounds, pyrazolynobenzimidazole series compounds, pyrazolotriazole series compounds or the like may be employed, as required, together with the magenta-dye-forming couplers of the invention.

Additionally, pyrazoloazole type couplers other than the magenta couplers of the invettion may be also combinedly employed. For this purpose, the examples disclosed in Japanese Patent O.P.I. Publications Nos. 162548/1984, 171956/1985, 33552/1985, 436593/1985 and 1919253/1985 and the like are available.

In relation to the method for incorporating the magenta coupler of the invention into the silver halide photographic light-sensitive material, those methods used for conventional magenta and other dye-forming couplers are similarily applicable. The most favorable method is to form the silver halide photographic light-sensitive material by incorporating the magenta coupler of the invention dissolved in a solvent into a silver halide emulsion which is coated upon a support. Such a silver halide photographic light-sensitive material may be whichever of a monochrome or multicolored type. If the similar material is of a multicolored type, the magenta coupler the invention is principally contained in a green-sensitive emulsion. However, the similar coupler may be contained within a non-sensitized emulsion layer or within an emulsion layer having a phtosensitivity in the trichromatic area of spectrum other than green color.

Each constituent to form the dye-image of the invention comprises a single emulsion layer or a plurality of emulsion layers, each layer being photo-sensitive to a certain area of spectrum.

The layers, including the layers of the above-mentioned image-forming constituent necessary for the silver halide photographic light-sensitive material can be disposed in the varous orders known in the photographic art. The typical multi-colored silver halide photographic light-sensitive material has a support, thereupon disposed are a cyan-dye-image-forming constituent comprising at least one red-sensitive silver halide emusion layer containing at least one cyan-dye-forming coupler, a magenta-dye-image-forming constituent comprising at least one green-sensitive silver halide emulsion layer containing at least one magenta-dye-forming-coupler (at least one ma genta-dye-forming-coupler is the magenta coupler of the invention) and a yellow-dye-image-forming constituent comprising at least one blue-sensitive silver halide emulsion layer containing at least one yellow-dye-forming-coupler.

Such a photographic light-sensitive material may also have additional layers, such as a filter layer, an intermediate layer, a protective layer, a subbing layer and the like.

To make the magenta coupler of the invention as well as each of other couplers ocntained in the silver halide photographic light-sensitive material, the conventionally known methods can be used. For example, the silver halide emulsion used with the present invention can be prepared in the following manner: after the magenta coupler or each of other couplers is dissolved into a mixture solution comprising a known high-boiling solvent as well as a low-boiling solvent containing butyl acetate, butyl propionate or the like, the solution is mixed with aquenous gelatin; after the solution is emusified with an emulsifier such as a high speed rotating mixer. A colloid mil or an ultrosonic dispersing machine, it is incorporated into the silver halide. p The typical known high-boiling solventes include phthalic esters, for example, dibutylphthalate, dioctylphthalate and the like, phosphoric esters (tricresylphosphate, trioctylphosphate and the like), N-substituted acid amides such as amide N,N-diethyllauriate and the like.

When incorporating the magenta coupler of the invention as well as each of other couplers into the silver halide emulsion layer, each of them is usually added at the rate of approximately 0.01–2 mol, or, preferably, 0.03–0.5 mol per mol silver halide.

The silver halides used for the silver halide emulsion of the present invention are those arbitrarily used for conventional silver halide emulsions and include silver bromide, silver chloride, silver iodide, silver chlorobromide, silver chloroiodobromide and the like.

The silver halide emulsion comprising the silver halide emulsion layers according to the invention can be produced, in addition to the usually practiced preparation methods, by any methods including those disclosed in Japanese Patent Examined Publication No. 7772/1971. In other words, the methods are as follows: The preparation for so-called conversion emulsion, wherein an emulsion containing silver salt grains at least a part of which comprises silver salt whose solubility is greater than that of silver bromide, then at least a part of the grains is converted into silver bromide of silver iodobromide; The preparation for Lippman emusion which comprises fine paricle silver halide having an average particle size of less than 1 μm. Additionally, the silver halide emulsion used with the present invention can be chemically sensitized by independently or combinedly, according to requirements, by using, for example, the following: a sulfur sensitizer such as arylthiocarbamide, thiourea, cystine and the like; a either active or inactive selenium sensitizer; a reduction sensitizer such as stannous salt, polyamine and the like; a noble metal sensitizer such as gold sensitizer, more specifically, potassium aurithiocyanate, potassium chloroaurate, 2-aurosulfobenzthiazolemethylchloride and the like; sensitizer comprising water-soluble salt derived from ruthenium, rhodium, iridium and the like, and, more specifically, such as ammonium chloroparadate, potassium chloroplatinate, sodium chloroparadite, and the like.

Additionally, the known photographic additives may be incorporated into the silver halide emulsions used with the present invention. They are, for example, the photographic additives disclosed in "Research Disclosure", December 1978, No. 17643.

For the silver halide used with the present invention, the spectral sensitization is effected in order to provede light-sensitivity in the required light-sensitive wavelength by an optional appropriate sensitizing dye. Various sensitizing dyes are used as the similar spectral sensitizing dye. One of them may be independently used, or more than two of them may be combinedly used.

As a typical spectral sensitizing dye advantageously used in the invention, the cyanine dyes, merocyanine dyes or composite cyanine dyes disclosed in, for example, U.S. Pat. Nos. 2,269,234, 2,270,378, 2,442,710, 2,454,620 and 2,776,280 are available.

As the previously mentioned support used with the invention, the suitable one may be arbitrarily selected, in compliance with the usage of the photographic light-sensitive material, from the conventionally known materials such as a plastic film, plastic-laminated paper, baryta paper, synthesized paper and the like. Generally, the subbing is provided on each of these supports in order ot enhance adherence with the photographic emulsion layer.

After the exposure, various photographic treatments are carried out on the silver halide photographic light-sensitive material of the invention for the color developing treatment. The color developers advantageously used in the invention are those having an aromatic primary amine type dye-forming developing agent as a principal component. The typical examples of such a color developing agent include the p-phenylenediamine series agents such as diethyl-p-phenylenediamine hydrochloride, monomethyl-p-phenylenediamine hydrochloride, dimethyl-p-phenylendiamine hydrochloride, 2-amino-5-diethylaminotoluene hydrohydrochloride, 2-amino-5-(N-ethyl-N-dodecylamino)-toluene, 2-amino-5-(N-ethyl-N-$\beta$-methanesulfonamidethyl)aminotoluene sulfate, 4-(N-ethyl-N-$\beta$-methanesulfonamidethylamino)aniline, 4-(N-ethyl-N-$\beta$-fydroxyethylamino)aniline, 2-amino-5-(N-ethyl-$\beta$-methoxyethyl)aminotoluene and the like. These color developing agents are independently, or more than two of them are combinedly employed, and if necessary, employed together with a monochrome developing agent such as hydroquinone or the like. additionally, the color developing agent generally contains an alkali agent such as sodium hydroxide, ammonium hydroxide, sodium carbonate, sodium sulfite or the like, and may further contain various additives, for example, a halogenated alkali metal such as potassium bromide, a developing modifier such as hydrazino acid or the like.

The silver halide photographic light-sensitive material of the invention may contain within its hydrophilic colloid layers the previously mentioned color developing agent as a color developing agent itself or as a precursor of color developing agent. The precursor of color developing agent is a compound being capable of forming a color developing agent in the alkaline environments and is available in the form of a Shiff base type precursor derived from an aromatic aldehyde derivative, multivalent metal-ion complex precursor, imide phthalate derivative precursor, amide phosphate derivative precursor, sugar-amine reactant precursor or urethane type precursor. These precursors of aromatic primary amine color developing agent are disclosed, for example, in U.S. Pat. Nos. 3,342,599, 2,507,114, 2,695,234, 3,719,492, U.K. Pat. No. 803,783, Japanese Patent O.P.I. Publications Nos. 135628/1978, 79035/1979, Research Disclosure Nos. 151 59, 12146 and 13924.

An enough amount, for satisfactory color-forming in the course of development, of such an aromatic primary amine color developing agent or its precursor should be incorporated. Such an amount varies according to the type or the like of a light-sensitive material, however, is usually at the range of 0.1 to 5 mol, or, preferably, 0.5 to 3 mol per mol light-sensitive silver halide. These color developing agents or their precursors are whichever independently or combinedly employed. To distribute the above-mentioned compounds into the photographic light-sensitive material, they are so added into the material after being dissolved in an optional appropriate solvent such as water, methanol, ethanol, acetone or the like. Or, they may be added in the form of an emusified fluid dispersion using a high-boiling solvent such as dibutylphthalate, dioctylphthalate, tricresylphosphate or the like. Or, they may be mixed after being impregnated into a latex polymer in the manner described in Research Disclosure, No. 14850.

After the color developing treatment, the silver halide photographic light-sensitive material is usually subjected to bleaching and fixing, or bleach-fixing, and water-rinsing treatments. As a bleaching agent, various compounds are used. Among them, multivalent metal compounds, such as ferric (III), cobalt (III), stannic (II) and the like, especially, complex salts of these mulvalanet metal cations and organic acids, for example, metal complex salts derived from aminopolycarboxylic acids such as ethylenediaminetetraacetic acid, nitrilotriacetic acid, N-hydroxyethylenediaminediacetic acid and the like, as well as malonic acid, tartaric acid, maleic acid, diglycolic acid, dithiogylcolic acid and the like, or ferricyanate and dichromate are independently or combinedly employed in a proper combination.

With the silver halide photographic light-sensitive meterial containing the magenta coupler of the invention, the silver halide photographic light-sensitive material being capable of forming a magenta-dye-image being excellent in color form-properties and preservability can be provided.

EXAMPLES

The present invention is specifically described with the reference to Examples.

(EXAMPLE-1)

Each of the magenta couplers of the invention as well as the comparison couplers, each being listed in Table 1, was prepared at the rate of 0.1 mol per mol silver. Tricresylphosphate whose weight being the same as the coupler as well as ethyl acetate whose weight being the triple of the coupler were added to each coupler, which was then heated to 60° C. to dissolve them completely. The resultant solution was mixed with 1200 ml of 5% aquenous gelatin containing 120 ml of 5% aquenous alkanol B (alkylnaphthalenesulfonate, manufactured by Dupont), whereby being emulsified and dispersed with an ultrasonic dispersing machine in order to provide an emulsified material. Next, the fluid dispersion was added into 4 kg of a green-sensitive silver iodo-bromide emulsion containing 6 mol % silver iodide, into which 120 ml 2% (water:methanol=1:1) 1,2bis(vinylsulfonyl)ethane was further added as a hardener. The solution was then coated on a subbed transparent polyester base and let to dry, thus preparing each sample (amount of coated silver: 20 mg/100 cm$^2$).

Each sample obtained in such a manner was subjected to exposure with optical wedge and to the following developing processed. The results are shown in Table 1.

| (Developing treatment) | | |
|---|---|---|
| Color developing | 38° C. | 3 min 15 sec |
| Bleaching | 38° C. | 4 min 20 sec |
| Water-rinsing | 38° C. | 3 min 15 sec |
| Fixing | 38° C. | 4 min 20 sec |
| Water-rinsing | 38° C. | 3 min 15 sec |
| Stabilizing | 38° C. | 1 min 30 sec |
| Drying | 47–55° C. | 16 min 30 sec |

The oomposition of treating solution used in each process is as follows.

| [Composition of color developer] | |
|---|---|
| Potassium carbonate | 30 g |
| Sodium bicarbonate | 2.5 g |
| Potassium sulfite | 5 g |
| Sodium bromide | 1.3 g |
| Potassium iodide | 2 mg |
| Hydroxylamine sulfate | 2.5 g |
| Sodium chloride | 0.6 g |
| Sodium diethyleneaminepentaacetate | 2.5 g |
| 4-amino-3-methyl-Nethyl-N—(β-hydroxyethyl) aniline sulfate | 4.8 g |
| Potassium hydroxide | 1.2 g |

Water was added to prepare 1 l solution. And the pH of the solution was adjusted to 10.06 with potassium hydroxide or 20% sulfuric acid.

| [Composition of bleacher] | |
|---|---|
| Ammonium ferric ethylenediaminetetraacetate | 100 g |
| Ethylenediaminetetraacetic acid | 10 g |
| Ammonium bromide | 150 g |
| Glacial acetic acid | 40 ml |
| Sodium bromate | 10 g |

Water was added to prepare 1 l solution. And the pH of the solutoin was adjusted to 3.5 with aquenous ammonium or glacial acetic acid,

| (Composition of fixer) | |
|---|---|
| Ammonium thiosulfate | 180 g |
| Sodium sulfite anhydride | 12 g |
| Sodium metabisulfite | 2.5 g |
| Bisodium ethylenediaminetetraacetate | 0.5 g |
| Sodium carbonate | 10 g |

Water was added to prepare 1 l solution.

| (Composition of stabilizer) | |
|---|---|
| Formalin (37% aqueous solution) | 2 ml |
| Konidax (manufactured by Konishiroku Photo Industry Co., Ltd.) | 5 ml |

Water was added to prepare 1 l solution.

TABLE 1

| Sample No. | Coupler to be used | Relative sensitivity[1] | Maximum density | Formalin resistance[2] |
|---|---|---|---|---|
| 11 | Comparison coupler 1 | 100 | 2.63 | 81 |
| 12 | Comparison coupler 2 | 91 | 2.32 | 75 |
| 13 | Coupler of the invention (1) | 123 | 2.73 | 91 |
| 14 | Coupler of the invention (2) | 132 | 2.82 | 93 |
| 15 | Coupler of the invention (4) | 129 | 2.60 | 92 |

TABLE 1-continued

| Sample No. | Coupler to be used | Relative sensitivity[1] | Maximum density | Formalin resistance[2] |
|---|---|---|---|---|
| 16 | Coupler of the invention (16) | 112 | 2.51 | 92 |
| 17 | Coupler of the invention (35) | 113 | 2.53 | 93 |
| 18 | Coupler of the invention (36) | 118 | 2.59 | 92 |
| 19 | Coupler of the invention (37) | 125 | 2.83 | 93 |

[1] The relative sensitivity is the inverse number of the exposure which gives the density of fog + 0.19. It was assumed that the similar sensitivity of sample 11 containing comparison coupler 1 is 100.
[2] After being left in an enclosure, which was controlled to have a temperature of 30° C. and a relative humidity of 62% and was provided with six ml of 0.9% aquenous formalin, for three days, each sample was subjected to color development. For comparison purpose, a sample not treated with formalin was also developed.

Formalin resistance = $\frac{\text{Coloring density of formalin-treated sample}}{\text{Coloring density of non-formalin-treated sample}} \times 100$ (%)

Comparison coupler 1

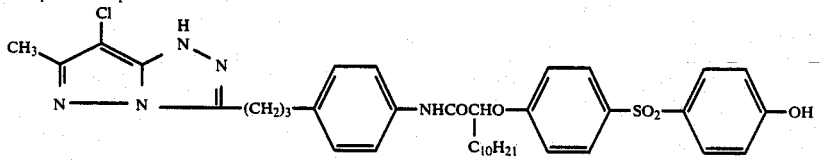

Comparison coupler 2

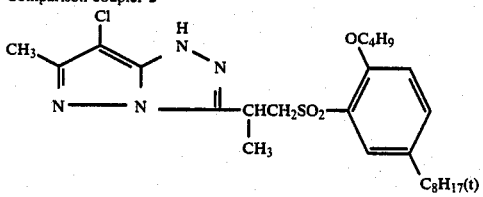

With this example, as can be understood from Table 1, the couplers of the invention (samples 13~19) have, when compared to the comparison couplers (samples 11 and 12), sufficiently advantageous color forming properties and are by far excellent in formalin resistance. The color forming properties of the coupler are represented by the maximum density and the sensitivity of the sample.

[EXAMPLE-2]

The samples 11~19, in Example-1 were likewise subjected to wedge exposure, then to the following developing processes. The results are shown in Table 2.

| [Developing treatment] | | |
|---|---|---|
| Color developing | 38° C. | 3 min 30 sec |
| Bleach-fixing | 38° C. | 1 min 30 sec |
| Stabilizing or water-rinsing | 25–30° C. | 3 min |
| Drying | 75–80° C. | approx. 2 min |

The composition of treating solution used in each process is as follows.

| [Composition of color developer] | |
|---|---|
| Benzyl alcohol | 15 ml |
| Ethylene glycol | 15 ml |
| Potassium sulfite | 2.0 g |
| Potassium bromide | 0.7 g |
| Sodium chloride | 0.2 g |
| Potassium carbonate | 30.0 g |
| Hydroxylamine sulfate | 3.0 g |
| Polyphosphoric acid (TPPS) | 2.5 g |
| 3-methyl-4-amino-N—ethyl-N—(β-methanesulfon-amidethyl)-aniline sulfate | 5.5 g |
| Fluorescent brightener (4,4'-diaminosulfonbenzsulfonic derivative) | 1.0 g |
| Potassium hydroxide | 2.0 g |

Water was added to prepare 1 solution whose pH was adjusted to 10.20.

| [Bleach-fixer] | |
|---|---|
| Ammonium ferric ethylenediaminetetraacetate dihydrate | 60 g |
| Ethylenediaminetetraacetic acid | 3 g |
| Ammonium thiosulfate (70% solution) | 100 ml |
| Ammonium sulfite (40% solution) | 27.5 ml |

Potassium carbonate or glacial acetic acid was used to adjust the pH to 7.1, whereby water was poured into to prepare 1 l solution.

| [Stabilizer] | |
|---|---|
| 5-chloro-2-methyl-4-isothiazoline-3-one | 1.0 g |
| Ethylene glycol | 10 g |

TABLE 2

| Sample No. | Coupler to be used | Relative sensitivity (1) | Maximum density | Light fastness (2) |
|---|---|---|---|---|
| 2-11 | Comparison coupler 1 | 100 | 2.40 | 22 |
| 2-12 | Comparison coupler 2 | 88 | 2.01 | 61 |
| 2-13 | Coupler of the invention (1) | 116 | 2.43 | 59 |
| 2-14 | Coupler of the invention (2) | 126 | 2.61 | 63 |
| 2-15 | Coupler of the invention (4) | 119 | 2.49 | 65 |
| 2-16 | Coupler of the invention (16) | 108 | 2.40 | 53 |
| 2-17 | Coupler of the invention (35) | 107 | 2.36 | 61 |
| 2-18 | Coupler of the invention (36) | 113 | 2.42 | 57 |
| 2-19 | Coupler of the invention (37) | 118 | 2.50 | 65 |

(1) The relative sensitivity is the inverse number of the exposure which gives the density of fog + 0.11. It was assumed that the similar sensitivity of sample 2-11 containing comparison coupler 1 is 100.
(2) After color developing treatment, each sample was exposed to a xenon fade meter for five days. The dye residual % of post-treatment sample was measured, under the assumption the initial density was D = 1.0.

Light fastness = $\frac{\text{Density after five-day exposure to a xenon fade meter}}{1.0} \times 100$ With this example, as can be understood from Table 2, the couplers of the invention (samples 2-13-2-19) are, when compared with the comparison couplers (samples 2-11 and 2-12), satisfactory in terms of both color forming properties and light fastness.

[EXAMPLE-3]

By sequentially disposing the following layers upon a polyethylene resin-coated paper containing titanium oxide, the silver halide colo photographic light-sensitive material was prepared.

The following amounts to be incorporated are those per 100 cm².

(1) A layer containing 20 mg gelatin, 5 mg blue-sensitive silver chloro-bromide emulsion in silver terms, and 3 mg di-octylphthalate coupler solvent into which 8 mg Y-coupler* as well as 0.1 mg 2,5-dit-octylhydroquinone having been dissolved.

(2) An intermediate layer containing 12 mg gelatin, and 2 mg dibutylphthalte ultraviolet-ray absorvent solvent into which 0.5 mg 2,5-di-t-octylhydroquinone as well as 4 mg ultravioletray absorvent having been dissolved.

(3) A layer containing 18 mg gelatin, 4 mg green-sensitive silver chloro-bromide emulsion in silver terms, and 2.5 mg dioctylphthalate coupler solvent into which 5 mg M-coupler*, 2 mg antioxidant* and 0.2 mg 2,5-di-t-octylhydroquinone having been dissolved.

(4) An intermediate layer containing the same components as (2).

(5) A layer containing 16 mg gelatin, 4 mg red-sensitive silver chloro-bromide emulsion in silver terms, and 2.0 mg tricresylphosphate coupler solvent into which 3.5 mg C-coupler* as well as 0.1 mg 2,5-di-t-octylhydroquinone having been dissolved.

(6) A gelatin protective layer containing 9 mg gelatin.

As an ultraviolet-ray abservent in layers (2) and (4), UV-1 and UV-2 respectively having the following structure were combinedly used.

As an antioxidant in layer (3), di-t-pentylhydroquinonedi-octylether was used.

The above-mentioned multi-layered light-sensitive material was treated in the same manner as Example-2. Table 3 lists Y-coupler, M-coupler and C-coupler respectively used in corresponding layer, and the results thereof. The magenta image density of each sample was measured, after each sample being subjected to white-light exposure.

The relative sensitivity and the light fastness were measured through the same method as Example 2.

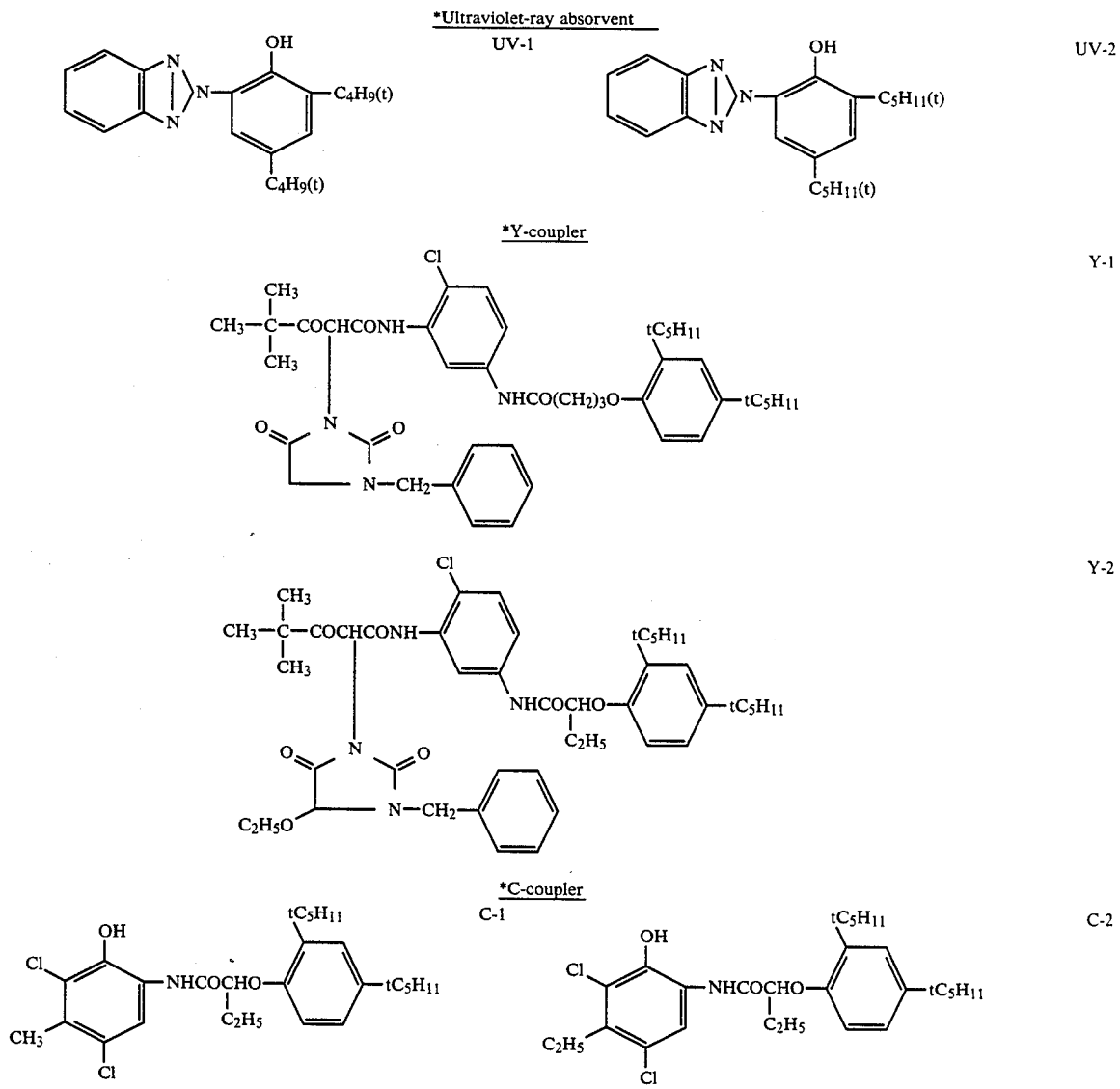

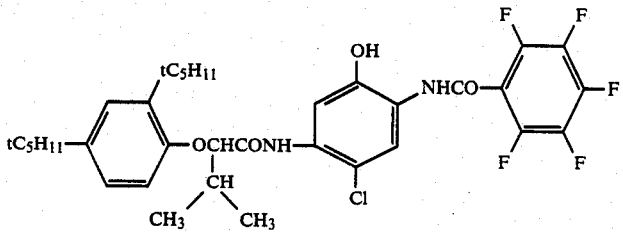

C-3

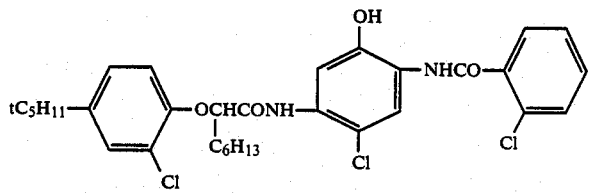

C-4

TABLE 3

| Sample No. | Layer (1) Y-coupler | Layer (3) M-coupler | Layer (5) C-coupler | Layer (5) Ultraviolet-ray absorbent | Relative sensitivity | Maximum density | Light fastness | Remarks |
|---|---|---|---|---|---|---|---|---|
| 31 | Y-1 | Comparison coupler (1) | C-1 | — | 100 | 2.30 | 25 | |
| 32 | Y-1 | Comparison coupler (1) | C-1 | UV-1 UV-2 | 101 | 2.29 | 37 | 2 mg ultraviolet-ray absorbent being incorporated into layer (5) |
| 33 | Y-1 | Coupler of the invention (38) | C-1 | — | 106 | 2.38 | 78 | |
| 34 | Y-1 | Coupler of the invention (38) | C-1 | UV-1 UV-2 | 105 | 2.32 | 87 | |
| 35 | Y-2 | Coupler of the invention (38) | C-2 | UV-1 UV-2 | 105 | 2.31 | 86 | |
| 36 | Y-2 | Coupler of the invention (38) | C-2 | UV-1 UV-2 | 100 | 2.28 | 95 | Layer identical to layer (2) being disposed between layers (5) and (6) in sample 35 by means of coating |
| 37 | Y-1 | Coupler of the invention (38) | C-3 | UV-1 UV-2 | 102 | 2.34 | 84 | |
| 38 | Y-1 | Coupler of the invention (38) | C-3 | UV-1 UV-2 | 104 | 2.36 | 93 | Layer structure being identical to that of sample 36 |
| 39 | Y-2 | Coupler of the invention (38) | C-4 | UV-1 UV-2 | 103 | 2.28 | 84 | |
| 40 | Y-2 | Coupler of the invention (38) | C-1 | UV-1 UV-2 | 104 | 2.36 | 85 | |
| 41 | Y-1 | Coupler of the invention (24) | C-1 | UV-1 UV-2 | 100 | 2.31 | 93 | |

With this example, as can be understood from Table 3, the couplers of the invention (samples 33–41) have, when compared to the comparison couplers (samples 31 and 32), sufficiently advantageous color forming properties and are by far excellent in light fastness of a dye-image.

[EXAMPLE 4]

Sample 51 was prepared by sequentaally coating the following layers upon a transparent support comprising a subbed cellulose triacetate. (Hereinafter, the amounts to be incorporated into the silver halide photographic light-sensitive material refer those per m², and the amounts of silver halide emulsion and colloid silver are indicated by the values converted to equivalent silver.)

Sample 51

Layer 1: An anti-halation layer containing 0.3 g black coloid silver and 2 g gelatin.
Layer 2: An intermediate layer containing 1.0 g gelatin.
Layer 3: A low-sensitivity red-sensitive silver iodo-bromide emulsion layer containing 1.5 g silver iodo-bromide which has an average particle size of 0.6 μm and includes 7 mol % silver iodide. [Containing 1.5 g gelatin, and 0.6 g H-1 into which 0.9 g cyan coupler (C-1), 0.07 g colored cyan coupler (CC-1) and 0.02 g DIR compound (W-2) having been dissolved.]
Layer 4: A high-sensitivity red-sensitive silver iodo-bromide emulsion layer containing 1.5 g silver iodo-bromide which has an average particle size of 1.2 μm and includes 8 mol % silver iodide. [Containing 1.5 g gelatin, and 0.20 g H-1 into which 0.17 g cyan coupler (C-1), 0.03 g colored cyan coupler (CC-1) and 0.02 g DIR compound (W-2) having been dissolved.]
Layer 5: An intermediate layer identical to layer 2.
Layer 6: A low-sensitivity green-sensitive silver iodo-bromide emulsion layer containing 1.5 g silver iodo-bromide which has an average particle size of 0.6 μm and includes 7 mol % silver iodide. [Containing 1.5 g gelatin, and 0.95 g H-1 into which 0.8 g magenta coupler (M-1), 0.12 g colored magenta coupler (CM-1) and 0.02 g DIR compound (W-2) having been dissolved.]
Layer 7: A high-sensitivity green-sensitive silver iodo-bromide emulsion layer containing 1.5 g silver iodo-bromide which has an average particle size of 1.2 μm and includes 8 mol % silver iodide. [Containing 1.5 g gelatin, and 0.3 g H-1 into which 0.17 g magenta coupler (M-1), 0.05 g colored magenta coupler (CM-1) and 0.02 g DIR compound (W-2) having been dissolved.]
Layer 8: A yellow filter layer containing 0.06 g H-2 into which 0.1 g yellow coloid silver and 0.1 g anti-staining agent (HQ-1) having been dissolved, as well as 1.5 gelatin.

Layer 9: A low-sensitivity blue-sensitive silver iodobromide emulsion layer containing 0.9 g silver iodo bromide which has an average particle size of 0.6 μm and includes 7 mol % silver iodide. [Containing 1.0 g gelatin, and 0.3 g H-1 into which 1.5 g yellow coupler (Y-1), 0.06 g DIR compound (W-1) having been dissolved.]

Layer 10: A high-sensitivity blue-sensitive silver iodobromide emulsion layer containing 1.0 g silver iodo bromide which has an average particle size of 1.2 μm and includes 8 mol % silver iodide. [Containing 1.0 g gelatin, and 0.06 g H-1 into which 0.3 g yellow coupler (Y-1), 0.06 g DIR compound (W-1) having been dissolved.]

Layer 11: A protective layer containing 1.5 g gelatin.

Sample 52 was prepared in the same manner as sample 51 except that M-1 in layers 6 and 7 of sample 51 was replaced with coupler 2 of the invention.

The formulas of the compounds employed are as follows.

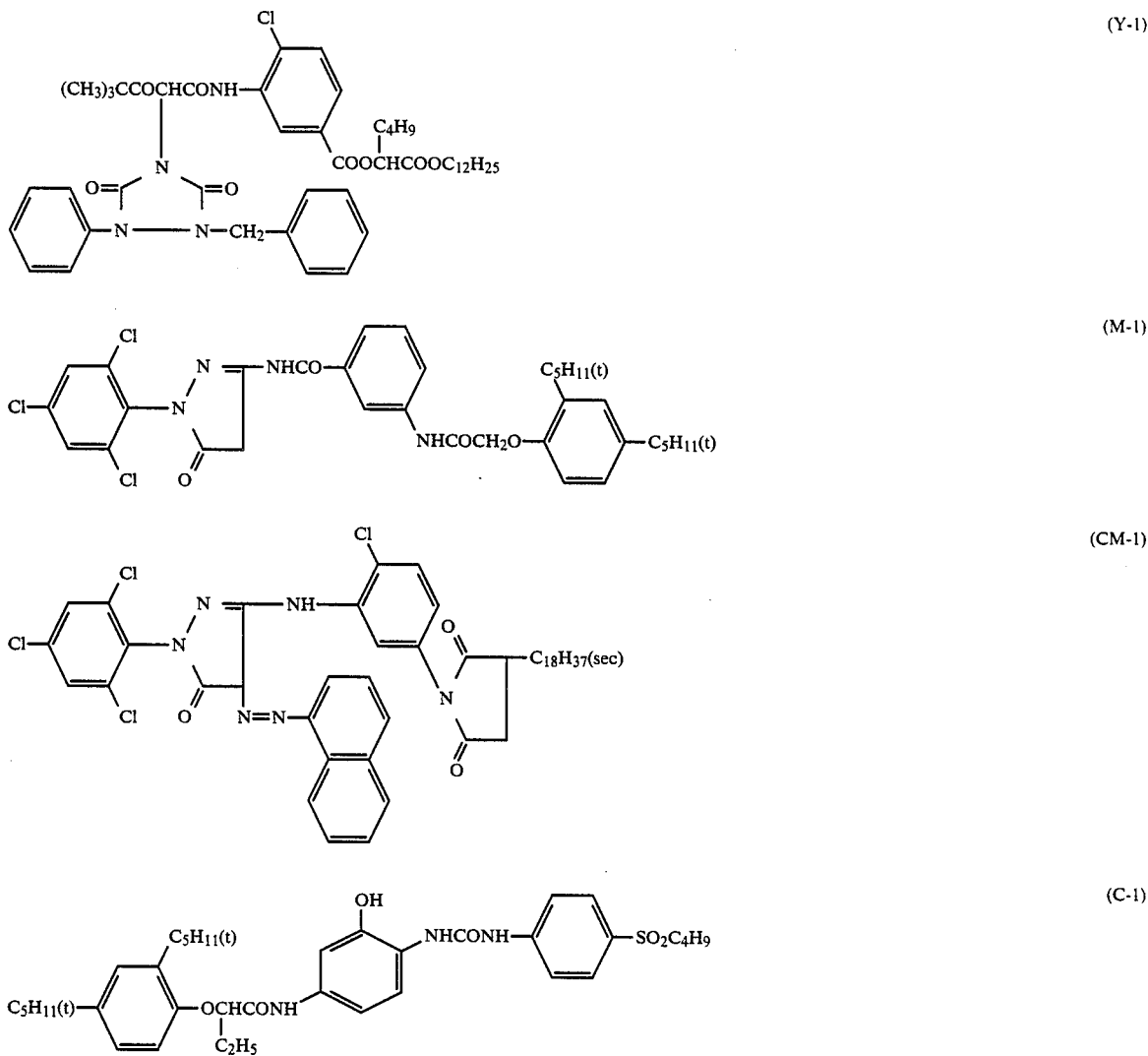

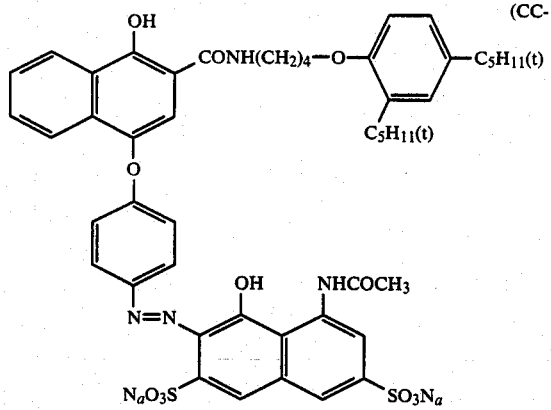 (CC-1)

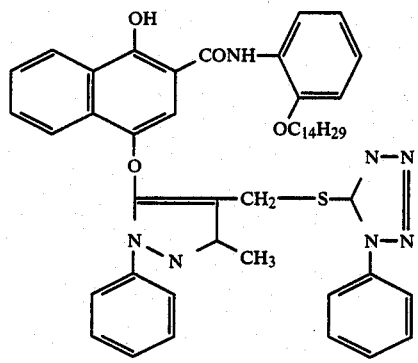 (W-2)

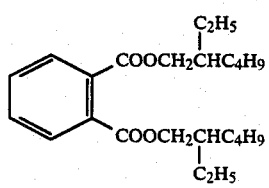 (H-2)

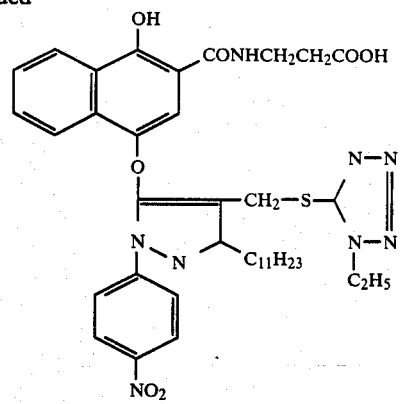 (W-1)

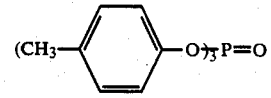 (H-1)

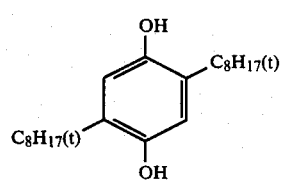 (HQ-1)

After these samples, 51 and 52 were subjected to white-light exposure, the formalin resistance of magenta image was determine in the same manner as the determination of formalin resistance in Example-1. The results are shown in Table 4.

TABLE 4

| Sample No. | Magenta coupler to be used | Formalin resistance or magenta image |
|---|---|---|
| 51 | M-1 | 53% |
| 52 | Coupler of the invention (2) | 95% |

As can be understood from Table 4, the light-sensitive material having extremely excellent formalin resistance was obtained by using the magenta coupler of the invention.

Also, as can be understood from the above-mentioned Examples 1 through 4, the light-sensitive material being capable of forming a magenta-dye-image excelling in color forming properties as well as preservability including formalin resistance, light fastness and the like can be provided by using the magenta coupler of the invention.

What is claimed is:

1. A silver halide light-sensitive material comprising a support and at least one silver halide emulsion layer provided thereon, wherein said emulsion layer contains a 1H-pyrazolo[3,2-c]-s-triazole type magenta coupler having an —SO$_2$—group in the third or sixth position of the coupler and at least one group selected from the group consisting of a —COOM group and a —SO$_3$M group in the third or sixth position of the coupler, M being a hydrogen atom or a cation, in the molecule thereof.

2. The silver halide light-sensitive material of claim 1, wherein said magenta coupler is represented by formula (I) or (II).

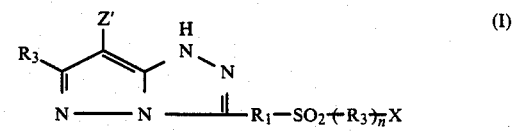 (I)

wherein R$_1$ and R$_2$ are each a bivalent group, R$_3$ is a hydrogen atom, an alkyl group, an aryl group, an alkylthio group, an acyl group, an alkoxy group,

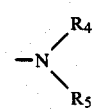

or a heterocyclic group, R$_4$ and R$_5$ are each an alkyl group or an aryl group, X is a monovalent group having said —COOM group or said —SO₃M group, $Z_1$ is a group capable of being split off from the coupler residue upon reaction of the coupler residue with an oxidized product of a color developing agent and n is 0 or 1,

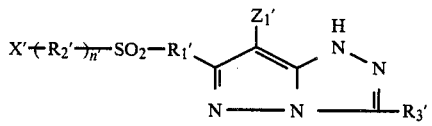 (II)

wherein $R_1'$, $R_2'$, $R_3'$, $X'$, $Z_1'$, and $n'$, are the same as $R_1$, $R_2$, $R_3$, $X$, $Z_1$ and n in formula (I), respectively.

3. The silver halide photographic light-sensitive material of claim 2, wherein $R_1$ and $R_2'$ are each an alkylene group having one to five carbon atoms.

4. The silver halide photographic light-sensitive material of claim 2, wherein $R_2$ and $R_2'$ are each group.

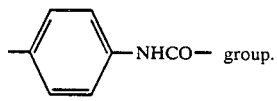

5. The silver halide photographic light-sensitive material of claim 2, an amount of said magenta coupler in said emulsion layer is from 0.01 to 2 mol per mol of silver contained in said emulsion layer.

* * * * *